(12) United States Patent
Khosla et al.

(10) Patent No.: US 8,535,946 B2
(45) Date of Patent: Sep. 17, 2013

(54) BIOMARKER TO MEASURE DRUG EFFICACY IN ENTEROPATHIC DISEASE

(75) Inventors: Chaitan Khosla, Palo Alto, CA (US); Michael Bethune, Pasadena, CA (US)

(73) Assignee: The Board of Trustees of the Leland Stanford Junior University, Palo Alto, CA (US)

( * ) Notice: Subject to any disclaimer, the term of this patent is extended or adjusted under 35 U.S.C. 154(b) by 140 days.

(21) Appl. No.: 12/677,501

(22) PCT Filed: Aug. 28, 2008

(86) PCT No.: PCT/US2008/010238
§ 371 (c)(1),
(2), (4) Date: Oct. 22, 2010

(87) PCT Pub. No.: WO2009/035510
PCT Pub. Date: Mar. 19, 2009

(65) Prior Publication Data
US 2011/0027897 A1 Feb. 3, 2011

Related U.S. Application Data

(60) Provisional application No. 60/971,435, filed on Sep. 11, 2007.

(51) Int. Cl.
*G01N 33/50* (2006.01)
*G01N 33/48* (2006.01)
(52) U.S. Cl.
USPC .................. 436/93; 436/63; 436/96; 436/98; 424/9.2
(58) Field of Classification Search
USPC ................ 436/63, 86, 93, 96, 98; 435/4, 7.1, 435/29; 424/9.2
See application file for complete search history.

(56) References Cited

U.S. PATENT DOCUMENTS

2003/0091975 A1 5/2003 Leyland-Jones
2003/0108938 A1 6/2003 Pickar et al.
2005/0239061 A1 10/2005 Marshall et al.

OTHER PUBLICATIONS

Chung; et al., "Pharmacokinetics and Drug Disposition: Comparison of midazolam and simvastatin as cytochrome P450 3A probes", Clinical Pharmacology & Therapeutics (2006), 79(4):350-61.
Gorski; et al., "Pharmacokinetics and Drug Disposition: The contribution of intestinal and hepatic CYP3A to the interaction between midazolam and clarithromycin", Clinical Pharmacology & Therapeutics (1998), 64(2):133-43.
Granvil; et al., "Expression of the human CYP3A4 gene in the small intestine of transgenic mice: in vitro metabolism and pharmacokinetics of midazolam", Drug Metabolism and Disposition (2003), 31(5):548-58.

Johnson; et al., "Enterocytic CYP3A4 in a paediatric population: developmental changes and the effect of coeliac disease and cystic fibrosis", J. Clin. Pharmacol. (2001), 51:451-60.
Kanazawa; et al., "Determination of midazolam and its metabolite as a probe for cytochrome P450 3A4 phenotype by liquid chromatography-mass spectrometry", Journal of Chromatography A (2004), 1031(1-2):213-8.
Kolars; et al., "Identification of Rifampin-inducible P450IIIA4 (CYP3A4) in Human Small Bowel Enterocytes", The Journal of Clinical Investigation (1992), 90:1871-8.
Lang; et al., "Decreased intestinal CYP3A in celiac disease: Reversal after successful gluten-free diet: A potential source of interindividual variability in first-pass drug metabolism", Clinical Pharmacology & Therapeutics (1996), 59 (1):41-6.
Langmann; et al., "Loss of detoxification in inflammatory bowel disease", Nature Clinical Practice Gastroenterology & Hepatology (2006), 3(7):358-9.
Lown; et al., "Grapefruit Juice Increases Felodipine Oral Availability in Humans by Decreasing Intestinal CYP3A Protein Expression", J. Clin. Invest. (1997), 99(10):2545-53.
Marsh; et al., "Morphology of the mucosal lesion in gluten sensitivity", Bailliere's Clinical Gastroenterology (1995), 9 (2):273-93.
Obach; et al., "Measurement of Michaelis Constants for Cytochrome P450-Mediated Biotransformation Reactions using a Substrate Depletion Approach", Drug Metabolism and Disposition (2002), 30(7):831-7.
Paine; et al., "First-pass metabolism of midazolam by the human intestine", Clinical Pharmacology & Therapeutics (1996), 60(1):14-24.
Piantadosi, "Clinical Trials: A Methodologic Perspective", Second Edition, John Wiley & Sons, Inc. (1997), pp. 36, 119, and 528.
Thummel; et al., "Oral first-pass elimination of midazolam involves both gastrointestinal and hepatic CYP3A-mediated metabolism", Clinical Pharmacology & Therapeutics (1996), 59(5):491-502.
Tsunoda; et al., "Differentiation of intestinal and hepatic cytochrome P450 3A activity with use of midazolam as an in vivo probe: Effect of ketoconazole", Clinical Pharmacology & Therapeutics (1999), 66(5):461-71.
Yokoyama; et al., "Simultaneous determination of creatinine, creatine, and UV-absorbing amino acids using dual-mode gradient low-capacity cation-exchange chromatography", Journal of Chromatography A (2005), 1085:110-6.

*Primary Examiner* — Maureen Wallenhorst
(74) *Attorney, Agent, or Firm* — Bozicevic, Field & Francis LLP; Pamela J. Sherwood

(57) ABSTRACT

The response of a patient with an enteropathic disease to therapy, particularly a candidate therapy in a clinical trial setting, is assessed by detecting the ability of the patient to metabolize an orally administered CYP3A substrate. The CYP3A metabolism may be monitored in a variety of ways. Conveniently, the appearance of a metabolite of the CYP3A substrate is detected in a patient sample over a period of time following oral administration, e.g. in urine, plasma, breath, saliva, etc. The CYP3A substrate is optionally labeled, e.g. with an isotopic, fluorescent, etc. label.

15 Claims, No Drawings

BIOMARKER TO MEASURE DRUG EFFICACY IN ENTEROPATHIC DISEASE

GOVERNMENT RIGHTS

This invention was made with Government support under Contract R01 DK063158 awarded by the National Institutes of Health. The Government has certain rights in this invention.

Cytochrome P450 enzymes are a heme-containing family that play central roles in oxidative, peroxidative and reductive metabolism of numerous endogenous and exogenous compounds, including many pharmaceutical agents. Substances known to be metabolized by P450 enzymes include steroids, bile acids, fatty acids, prostaglandins, leukotrienes, biogenic amines, retinoids, lipid hydroperoxides, phytoalexins, pharmaceuticals, environmental chemicals and pollutants. P450 substrates also include natural plant products involved in flavor, odor, flower color, and the response to wounding. P450 enzymes and other drug-metabolizing enzymes maintain steady-state levels of endogenous ligands involved in ligand-modulated transcription of genes effecting growth, apoptosis, differentiation, cellular homeostasis, and neuroendocrine functions. The metabolism of foreign chemicals by P450 enzymes can produce toxic metabolites, some of which have been implicated as agents responsible for birth defects and tumor initiation and progression.

The CYP3A subclass catalyzes a remarkable number of oxidation reactions of clinically important drugs such as quinidine, warfarin, erythromycin, cyclosporin A, midazolam, lidocain, nifedipine, and dapsone. Current estimates are that more than 60% of clinically used drugs are metabolized by the CYP3A4 enzyme, including such major drug classes as calcium channel blockers, immunosuppressants, macrolide antibiotics and anticancer drugs.

In addition to the liver, the P450s are expressed appreciably in the small intestinal mucosa, lung, kidney, brain, olfactory mucosa, and skin. Of these tissues, the intestinal mucosa is the most important extrahepatic site of drug biotransformation. As a consequence, the potential exists for substantial presystemic metabolism and thus an enhanced reduction in bioavailability as a drug passes, sequentially, through the small intestine and liver. See Lang et al. (1996) Clin Pharmacol Ther 59:41-46; Kolars et al. (1992) J. Clin. Invest. 90:1871-1878, herein specifically incorporated by reference.

As in the liver, CYP3A is the most abundant P450 subfamily expressed in the small intestine, with an average (or median) specific content representing from 50 to 70% of spectrally determined P450 content. Like hepatic CYP3A, enteric CYP3A is localized in a single cell type, specifically, within the mature absorptive columnar epithelial cells (enterocytes) that largely compose the mucosal lining. Enteric microsomal CYP3A content, as well as associated catalytic activity, is generally highest in the proximal region and then declines sharply toward the distal ileum.

Although the total mass of CYP3A in the entire small intestine has been estimated to be ~1% of that in the liver, human studies have demonstrated that enteric CYP3A can contribute significantly, and in some cases equally with hepatic CYP3A, to the overall first-pass metabolism of several drugs, particularly those are absorbed by the transcellular route. An advantage of CYP3A activity as a biomarker for enteropathy is the rapidity with which CYP3A activity can change. For example, as little as 7 days of treatment with rifampin, a known inducer of CYP3A4, can result in a >5-fold increase in enzyme activity in the small intestine (Kolars, et al, vide supra). Similarly, grapefruit juice, a known down-regulator of CYP3A4, reduces the small bowel epithelial concentration of this enzyme by >2-fold in as little as 6 days (Lown, et al., *J. Clin. Invest.* 99, 2545, 1997). Thus, it is possible to minimize the duration of illness in patients in whom disease must be induced for diagnostic or related purposes.

A number of disease conditions involve enterocytes. For example, in 1953, it was first recognized that ingestion of gluten, a common dietary protein present in wheat, barley and rye causes disease in sensitive individuals. Gluten is a complex mixture of glutamine- and proline-rich glutenin and gliadin molecules, which is thought to be responsible for disease induction. Ingestion of such proteins by sensitive individuals produces flattening of the normally luxurious, rug-like, epithelial lining of the small intestine known to be responsible for efficient and extensive terminal digestion of peptides and other nutrients.

Clinical symptoms of Celiac Sprue include fatigue, chronic diarrhea, malabsorption of nutrients, weight loss, abdominal distension, anemia, as well as a substantially enhanced risk for the development of osteoporosis and intestinal malignancies (lymphoma and carcinoma). The disease has an incidence of approximately 1 in 200 in most populations. Although no non-dietary therapy has been approved thus far for the treatment of Celiac Sprue, several efforts are under way to develop oral enzyme therapies (hereafter referred to as "glutenases") that accelerate the digestion, detoxification and assimilation of proteolytically resistant, immunotoxic gluten peptides in the celiac patient's gastrointestinal tract. Other types of drugs are also being considered for treatment of celiac sprue.

A related disease is dermatitis herpetiformis, which is a chronic eruption characterized by clusters of intensely pruritic vesicles, papules, and urticaria-like lesions. IgA deposits occur in almost all normal-appearing and perilesional skin. Asymptomatic gluten-sensitive enteropathy is found in 75 to 90% of patients and in some of their relatives. Onset is usually gradual. Itching and burning are severe, and scratching often obscures the primary lesions with eczematization of nearby skin, leading to an erroneous diagnosis of eczema. Strict adherence to a gluten-free diet for prolonged periods may control the disease in some patients, obviating or reducing the requirement for drug therapy. Dapsone, sulfapyridine and colchicines are sometimes prescribed for relief of itching, although the underlying disease is unaffected by these drugs. Given the close relationship between Celiac Sprue and dermatitis herpetiformis pathogenesis, the above-mentioned therapies are also expected to be useful for the treatment of dermatitis herpetiformis.

There is an urgent need for the development of sensitive, specific and non-invasive biomarkers for assessing drug efficacy in the treatment of patients with enteropathic diseases such as Celiac Sprue. The ideal biomarker would not only facilitate clinical trials of drug candidates, but would also find utility in disease management of patients who are prescribed such medications. Current diagnostic methods for Celiac Sprue, such as ELISA-based methods in which either anti-gliadin or anti-tTG antibodies in the patient's serum are detected or T cell methods in which cell proliferation or γ-IFN secretion is measured upon stimulation with gliadin, are unsuitable for this purpose. Antibody tests are unsuitable because patients must be exposed to relatively high doses of gluten over extended durations before they seroconvert. T cell proliferation assays are more sensitive, but they require invasive procedures (e.g. withdrawal of a small intestinal biopsy or relatively large quantities of blood to harvest adequate numbers of peripheral blood mononuclear cells) and are deemed to be too expensive for routine use. The present invention addresses this emerging but unmet medical need.

SUMMARY OF THE INVENTION

Methods are provided for diagnosis and clinical monitoring of enteropathic disease, which diseases include, without limitation, celiac sprue, Crohn's disease and irritable bowel syndrome. In some embodiments, the methods of the invention are used in determining the efficacy of a therapy for treatment of an enteropathic disease, either at an individual level, or in the analysis of a group of patients, e.g. in a clinical trial format. Such embodiments typically involve the comparison of two or more time points for a patient or group of patients. The patient status is expected to differ between the two time points as the result of administration of a therapeutic agent, therapeutic regimen, or challenge with a disease-inducing agent to a patient undergoing treatment. The response of a patient with an enteropathic disease to therapy is assessed by detecting the ability of the patient to metabolize an orally administered CYP3A substrate. The patient metabolism may be monitored in a variety of ways. Conveniently, the appearance of a metabolite of the CYP3A substrate is detected in a patient sample over a period of time following oral administration, e.g. in urine, plasma, breath, saliva, etc. The CYP3A substrate is optionally labeled, e.g. with an isotopic, fluorescent, etc. label.

Various formats may be used in the pharmacokinetic analysis. In some embodiments, a patient sample is obtained prior to treatment, as a control, and compared to samples from the same patient following treatment. In other embodiments, the CYP3A function is assessed over long periods of time to monitor patient status.

DETAILED DESCRIPTION

Enteropathic disease is clinically monitored by measuring the pharmacokinetic behavior of substances that are primarily metabolized by CYP3A cytochromes. In preferred embodiments such substances are orally administered, as a solution, enteric formulation, etc.

The pharmacokinetics of an orally administered drug CYP3A substrate is monitored as a non-invasive surrogate for enteropathy. Certain xenobiotic cytochrome P450 enzymes, such as CYP3A4, are highly active in enterocytes as well as liver cells (Kolars, 1992). However, in contrast to the liver, where the expression level is relatively constant, CYP3A4 levels can fluctuate significantly in the small bowel. For example, CYP3A4 is abundant in enterocytes near villous tips but not near the crypts (Kolars, 1992; Lang, 1996; Johnson, 2001), suggesting that CYP3A4 activity correlates with enterocyte maturity.

Dietary gluten is known to induce abnormal enterocyte morphology and physiology in celiac patients (Kagnoff, 2007). Consequently, celiac patients with active disease have decreased CYP3A protein and activity levels in their small intestine, both of which recover to normal after introduction of a gluten-free diet (Lang, 1996; Johnson, 2001). Thus, drug efficacy in celiac patients is conveniently monitored using intestinal CYP3A4 activity as a surrogate for gluten-induced enteropathy.

DEFINITIONS

As used herein, the term "therapeutic drug" or "therapeutic regimen" refers to an agent used in the treatment or prevention of a disease or condition, particularly an enteropathic condition for the purposes of the present invention. Of interest are clinical trials using such therapies, and monitoring of patients undergoing such therapy.

In some embodiments, the therapy involves treatment of celiac sprue patients with glutenase. In other embodiments, the therapy involves treatment of celiac sprue patients with a transglutaminase inhibitor. Assessment of treatment may utilize a gluten challenge. In some embodiments, 1-14 days of a moderate dose (at least about 1 g/day, at least about 5 g/day, at least about 10 g/day, or more) of oral gluten is utilized for this for this purpose. Patients may be control patients that have not been treated, or patients subject to a clinical regimen of interest, e.g. dietary restriction of gluten, treatment with transglutaminase inhibitor, treatment with glutenase, and the like.

A "patient," as used herein, describes an organism, including mammals, from which samples are collected in accordance with the present invention. Mammalian species that benefit from the disclosed systems and methods for therapeutic drug monitoring include, and are not limited to, apes, chimpanzees, orangutans, humans, monkeys; and domesticated animals (e.g., pets) such as dogs, cats, mice, rats, guinea pigs, and hamsters.

The term "pharmacokinetics," refers to the mathematical characterization of interactions between normal physiological processes and a therapeutic drug over time (i.e., body effect on drug). Certain physiological processes (absorption, distribution, metabolism, and elimination) will affect the ability of a drug to provide a desired therapeutic effect in a patient. Knowledge of a drug's pharmacokinetics aids in interpreting drug blood stream concentration and is useful in determining pharmacologically effective drug dosages The terms "cytochrome P450" and "CYP" are meant to refer to a large family (often called a "superfamily") of hemoprotein enzymes capable of metabolizing xenobiotics such as drugs, carcinogens, and environmental pollutants, as well as endobiotics such as steroids, fatty acids, and prostaglandins. As used herein, these terms are meant to encompass all members of the CYP superfamily. In some embodiments, these terms refer to CYPs of human origin.

All isoenzymes, or isoforms, within the CYP superfamily are contemplated to fall within the terms "cytochrome P450" and "CYP" as used herein. Particularly contemplated CYP isoforms include, but are not limited to, members of the CYP1A, CYP2B, CYP2C, CYP2D, CYP2E, and CYP3A families, as these isoforms have been identified as those most commonly responsible for the metabolism of drugs in humans.

CYP3A substrate. As used herein, the term refers to a compound that is enzymatically transformed by CYP3A into a different compound, or metabolite. For the purposes of the present invention, it is desirable for the primary metabolite or metabolites to be detectably different than the substrate. It is additionally desirable that the substrate by orally administered, and that it by absorbed in the gut.

A number of commercially available drugs are metabolized by CYP3A4 and may find use in the methods of the invention. Substrates of interest include, without limitation, those set forth in Table 1, with their primary metabolite(s).

TABLE 1

| Substrate | Primary Metabolite(s) |
|---|---|
| cyclosporine A | AM9[1] AM1[1] AM4N[1] |
| Midazolam | 1'-hydroxymidazolam, 4-hydroxymidozalam |
| Triazolam | 1'-hydroxytriazolam, 4-hydroxytriazalam |
| lovastatin | (β)-hydroxy acid form |

TABLE 1-continued

| Substrate | Primary Metabolite(s) |
| --- | --- |
| Simvastatin | 3'-hydroxy simvastatin, 6'-exomethylene simvastatin, 3',5'-dihydrodiol simvastatin, simvastatin (β)-hydroxy acid |
| Terfenadine | azacyclonol and terfenadine alcohol |

In some embodiments of the invention, midazolam is the CYP3A substrate. Midazolam exhibits large and relatively reproducible clearance rate changes in humans, most of which can be attributed to changes in enteric metabolism (Thummel et al. (1996) Clin. Pharm Therap. 59:491; Gorski et al. (1998) Clin. Pharm Therap. 64:133; Paine et al. Clin. Pharm Therap. 60:14-24; Chung et al. (2006) Pharmacokinetics & Drug Disposition 79:350, each herein incorporated by reference). Thus, by monitoring $C_{max}$, AUC or clearance rate of a single dose of midazolam, e.g. if midozalam is administered following a gluten challenge in the presence of drug or placebo, during long term treatment of a celiac patient, etc., the efficacy of the treatment is assessed. In humans, midazolam is primarily eliminated from the body by metabolism to 1'-hydroxymidazolam and 4-hydroxymidazolam by enzymes in the 3A subfamily of cytochrome P450, and less than 1% of the dose is excreted unchanged in the urine. Midazolam clearance and the 1'-hydroxymidazolam to midazolam plasma ratio after intravenous administration have proved to be effective indices of CYP3A activity in liver biopsies. Following oral administration, midazolam is useful in assessing enterocyte CYP3A function.

An alternative CYP3A4 substrate is oral simvastatin, the bioavailability of which is more dependent on intestinal metabolism than midazolam. Changes in intestinal CYP3A4 activity can be monitored with simvastatin by measuring serum concentration of the drug 1-2 hours post-dose, which reasonably approximates the Cmax of the drug. The advantage of a reliable single time-point measure of intestinal CYP3A4 activity is that a finger-stick or urine test can be used for long-term monitoring of compliance to a gluten-free diet or adherence to drug regimen.

The term "patient sample" or "sample" as used herein refers to a sample from an animal, most preferably a human, seeking diagnosis or treatment of a disease, e.g. an enteropathic disease. Samples of the present invention include, without limitation, urine, saliva, breath, and blood, including derivatives of blood, e.g. plasma, serum, etc.

Sample Analysis.

Patient samples are analyzed to determine the metabolism of a CYP3A substrate, usually an orally administered CYP3A substrate. Sample may be quantitatively analyzed for the presence of the substrate and/or its metabolites by any suitable assay, which are well-known in the art. Methods of analysis include liquid chromatography-mass spectroscopy (see Kanazawa et al. (2004) J. Chromatography 1031:213-218, Gorski et al., supra.); HPLC; ion-monitoring gas chromatography/mass spectroscopy (see Paine et al., supra.); gas chromatography; semiconductive gas sensors; immunoassays; mass spectrometers (including proton transfer reaction mass spectrometry), infrared (IR) or ultraviolet (UV) or visible or fluorescence spectrophotometers (i.e., non-dispersive infrared spectrometer); binding assays involving aptamers or engineered proteins etc.

In other embodiments, competitive binding immunoassays can be used to test a bodily fluid sample for the presence of the substrate or metabolites. Immunoassay tests may include an absorbent, fibrous strip having one or more reagents incorporated at specific zones on the strip. The bodily fluid sample is deposited on the strip and by capillary action the sample will migrate along the strip, entering specific reagent zones in which a chemical reaction may take place. At least one reagent is included which manifests a detectable response, for example a color change, in the presence of a minimal amount of a signaling agent of interest.

In some embodiments, the biological sample is patient breath. Sensors that can analyze a patient's exhaled breath components to detect, quantify, and/or trend concentrations of compounds in exhaled breath, can be correlated to the compound concentration in the patient's body, in particular in blood. A sensor can be selected from a variety of systems that have been developed for use in collecting and monitoring exhaled breath components, particularly specific gases. For example, the sensor of the subject invention can be selected from those described in U.S. Pat. Nos. 6,010,459; 5,081,871; 5,042,501; 4,202,352; 5,971,937, and 4,734,777. Further, sensor systems having computerized data analysis components can also be used in the subject invention (i.e., U.S. Pat. No. 4,796,639).

In other embodiments, the biological sample is patient urine. The concentration of the compound and its metabolites can be monitored in a 6-hour urine collection. In cases where any of these concentrations show a good correlation to the plasma AUC of the compound, a urine test can be developed for CYP3A activity using this biomarker.

Conditions of interest for monitoring methods of the present invention include a variety of enteropathic conditions, particularly chronic conditions. In some embodiments of the invention, a patient is diagnosed as having an enteropathic condition, for which treatment is contemplated. The patient may be initially tested for enteric CYP3A activity prior to treatment, in order to establish a baseline level of activity. Alternatively, the patient may be released from a treatment regimen for a period of time sufficient to induce an enteropathic state, in which state the patient is tested for enteric CYP3A activity in order to establish a baseline level of activity. Enteropathic conditions of interest include, without limitation, Celiac Sprue, herpetiformis dermatitis, irritable bowel syndrome (IBS); and Crohn's Disease.

Celiac sprue is an immunologically mediated disease in genetically susceptible individuals caused by intolerance to gluten, resulting in mucosal inflammation, which causes malabsorption. Symptoms usually include diarrhea and abdominal discomfort. Onset is generally in childhood but may occur later. No typical presentation exists. Some patients are asymptomatic or only have signs of nutritional deficiency. Others have significant GI symptoms.

Celiac sprue can present in infancy and childhood after introduction of cereals into the diet. The child has failure to thrive, apathy, anorexia, pallor, generalized hypotonia, abdominal distention, and muscle wasting. Stools are soft, bulky, clay-colored, and offensive. Older children may present with anemia or failure to grow normally. In adults, lassitude, weakness, and anorexia are most common. Mild and intermittent diarrhea is sometimes the presenting symptom. Steatorrhea ranges from mild to severe (7 to 50 g fat/day). Some patients have weight loss, rarely enough to become underweight. Anemia, glossitis, angular stomatitis, and aphthous ulcers are usually seen in these patients. Manifestations of vitamin D and Ca deficiencies (eg, osteomalacia, osteopenia, osteoporosis) are common. Both men and women may have reduced fertility.

The diagnosis is suspected clinically and by laboratory abnormalities suggestive of malabsorption. Family incidence is a valuable clue. Celiac sprue should be strongly considered in a patient with iron deficiency without obvious GI bleeding. Confirmation usually involves a small-bowel biopsy from the second portion of the duodenum. Findings include lack or shortening of villi (villous atrophy), increased intraepithelial cells, and crypt hyperplasia. Because biopsy results may be non-specific, serologic markers can aid diagnosis. Anti-gliadin antibody (AGA) and anti-endomysial antibody (EMA, an antibody against an intestinal connective tissue protein) in combination have a positive and negative predictive value of nearly 100%. These markers can also be used to screen populations with high prevalence of celiac sprue, including 1st-degree relatives of affected patients and patients with diseases that occur at a greater frequency in association with celiac sprue. If either test is positive, the patient may have a diagnostic small-bowel biopsy performed. If both are negative, celiac sprue is unlikely. Other laboratory abnormalities often occur and may be sought. These include anemia (iron-deficiency anemia in children and folate-deficiency anemia in adults); low albumin, Ca, K, and Na; and elevated alkaline phosphatase and PT. Malabsorption tests are sometimes performed, although they are not specific for celiac sprue. If performed, common findings include steatorrhea of 10 to 40 g/day and abnormal D-xylose and (in severe ileal disease) Schilling tests.

Conventional treatment is gluten-free diet (avoiding foods containing wheat, rye, or barley). Gluten is so widely used that a patient needs a detailed list of foods to avoid. Patients are encouraged to consult a dietitian and join a celiac support group. The response to a gluten-free diet is usually rapid, and symptoms resolve in 1 to 2 months. Ingesting even small amounts of food containing gluten may prevent remission or induce disease.

Complications include refractory sprue, collagenous sprue, and the development of intestinal lymphomas. Intestinal lymphomas affect 6 to 8% of patients with celiac sprue, usually presenting in the patient's 50s. The incidence of other GI malignancies (eg, carcinoma of the esophagus or oropharynx, small-bowel adenocarcinoma) increases. Adherence to a gluten-free diet can significantly reduce the risk of malignancy.

Dermatitis herpetiformis is a chronic eruption characterized by clusters of intensely pruritic vesicles, papules, and urticaria-like lesions. The cause is autoimmune. Diagnosis is by skin biopsy with direct immunofluorescence testing. Treatment is usually with dapsone or sulfapyridine.

This disease usually presents in patients 30 to 40 yr old and is rare in blacks and East Asians. It is an autoimmune disease. Celiac sprue is present in 75 to 90% of dermatitis herpetiformis patients and in some of their relatives, but it is asymptomatic in most cases. The incidence of thyroid disease is also increased. Iodides may exacerbate the disease, even when symptoms are well controlled. The term "herpetiformis" refers to the clustered appearance of the lesions rather than a relationship to herpesvirus.

Patients may have skin biopsy of a lesion and adjacent normal-appearing skin. IgA deposition in the dermal papillary tips is usually present and important for diagnosis. Patients should be evaluated for celiac sprue.

Strict adherence to a gluten-free diet for prolonged periods (eg, 6 to 12 mo) controls the disease in some patients, obviating or reducing the need for drug therapy. When drugs are needed, dapsone may provide symptomatic improvement. It is started at 50 mg po once/day, increased to bid or tid (or a once/day dose of 100 mg); this usually dramatically relieves symptoms, including itching, within 1 to 3 days; if so, that dose is continued. If no improvement occurs, the dose can be increased every week, up to 100 mg qid. Most patients can be maintained on 50 to 150 mg/day, and some require as little as 25 mg/wk. Although less effective, sulfapyridine may be used as an alternative for those who cannot tolerate dapsone. Initial oral dosage is 500 mg bid, increasing by 1 g/day q 1 to 2 wk until disease is controlled. Maintenance dosage varies from 500 mg twice/wk to 1000 mg once/day. Colchicine is another treatment option. Treatment continues until lesions resolve.

Crohn's Disease (Regional Enteritis; Granulomatous Ileitis or Ileocolitis) is a chronic transmural inflammatory disease that usually affects the distal ileum and colon but may occur in any part of the GI tract. Symptoms include diarrhea and abdominal pain. Abscesses, internal and external fistulas, and bowel obstruction may arise. Extraintestinal symptoms, particularly arthritis, may occur. Diagnosis is by colonoscopy and barium contrast studies. Treatment is with 5-aminosalicylic acid, corticosteroids, immunomodulators, anticytokines, antibiotics, and often surgery.

The most common initial presentation is chronic diarrhea with abdominal pain, fever, anorexia, and weight loss. The abdomen is tender, and a mass or fullness may be palpable. Gross rectal bleeding is unusual except in isolated colonic disease, which may manifest similarly to ulcerative colitis. Some patients present with an acute abdomen that simulates acute appendicitis or intestinal obstruction. About 33% of patients have perianal disease (especially fissures and fistulas), which is sometimes the most prominent or even initial complaint. In children, extraintestinal manifestations frequently predominate over GI symptoms; arthritis, fever of unknown origin, anemia, or growth retardation may be a presenting symptom, whereas abdominal pain or diarrhea may be absent.

With recurrent disease, symptoms vary. Pain is most common and occurs with both simple recurrence and abscess formation. Patients with severe flare-up or abscess are likely to have marked tenderness, guarding, rebound, and a general toxic appearance. Stenotic segments may cause bowel obstruction, with colicky pain, distention, obstipation, and vomiting. Adhesions from previous surgery also may produce bowel obstruction, which begins rapidly, without the prodrome of fever, pain, and malaise typical of obstruction due to a Crohn's disease flare-up. An enterovesical fistula may produce air bubbles in the urine (pneumaturia). Draining cutaneous fistulas may occur. Free perforation into the peritoneal cavity is unusual.

Crohn's disease should be suspected in a patient with inflammatory or obstructive symptoms or in a patient without prominent GI symptoms but with perianal fistulas or abscesses or with otherwise unexplained arthritis, erythema nodosum, fever, anemia, or (in a child) stunted growth. A family history of Crohn's disease also increases the index of suspicion. Patients presenting with an acute abdomen (either initially or on relapse) should have flat and upright abdominal x-rays and an abdominal CT scan. These studies demonstrate obstruction, abscesses or fistulas, and other possible causes of an acute abdomen (eg, appendicitis). Ultrasound may better delineate gynecologic pathology in women with lower abdominal and pelvic pain.

If initial presentation is less acute, an upper GI series with small-bowel follow-through and spot films of the terminal ileum is preferred over conventional CT. However, newer techniques of CT enterography, which combines high-resolution CT with large volumes of ingested contrast, are becoming the procedures of choice in some centers. These imaging studies are virtually diagnostic if they show characteristic strictures or fistulas with accompanying separation of bowel loops. If findings are questionable, CT enteroclysis or video capsule enteroscopy may show superficial aphthous and linear ulcers. Barium enema x-ray may be used if symptoms appear predominantly colonic (eg, diarrhea) and may show reflux of barium into the terminal ileum with irregularity, nodularity, stiffness, wall thickening, and a narrowed lumen. Differential diagnoses in patients with similar x-ray findings include cancer of the cecum, ileal carcinoid, lymphosarcoma, systemic vasculitis, radiation enteritis, ileocecal TB, and ameboma.

Established Crohn's disease is rarely cured but is characterized by intermittent exacerbations and remissions. Some patients suffer severe disease with frequent, debilitating periods of pain. However, with judicious medical therapy and, where appropriate, surgical therapy, most patients function well and adapt successfully. Disease-related mortality is very low. GI cancer, including cancer of the colon and small bowel, is the leading cause of excess Crohn's disease-related mortality.

5-Aminosalicylic acid (5-ASA, mesalamine) is commonly used as first-line treatment, although its benefits for small-bowel disease are modest at best. Antibiotics are considered a first-line agent by some clinicians, or they may be reserved for patients not responding to 4 wk of 5-ASA; their use is strictly empiric. With any of these drugs, 8 to 16 wk of treatment may be required. Patients with more severe disease may require corticosteroids, either oral or parenteral, depending on severity of symptoms and frequency of vomiting. Patients not responding to corticosteroids, or those whose doses cannot be tapered, should receive azathioprine, or possibly methotrexate. 6-mercaptopurine is preferred by some as a second-line agent after corticosteroids, and even as a first-line agent in preference to corticosteroids, but it is contraindicated in active uncontrolled infection.

Irritable bowel syndrome consists of recurring upper and lower GI symptoms, including variable degrees of abdominal pain, constipation or diarrhea, and abdominal bloating. Diagnosis is clinical. Treatment is generally symptomatic, consisting of dietary management and drugs, including anticholinergics and agents active at serotonin receptors.

There are no consistent motility abnormalities. Some patients have an abnormal gastro-colonic reflex, with delayed, prolonged colonic activity. There may be reduced gastric emptying or disordered jejunal motility. Some patients have no demonstrable abnormalities, and in those that do, the abnormalities may not correlate with symptoms. Small-bowel transit varies: sometimes the proximal small bowel appears to be hyperreactive to food or parasympathomimetic drugs. Intraluminal pressure studies of the sigmoid show that functional constipation can occur with hyperreactive haustral segmentation (ie, increased frequency and amplitude of contractions). In contrast, diarrhea is associated with diminished motor function. Thus strong contractions can, at times, accelerate or delay transit.

Hypersensitivity to normal amounts of intraluminal distention and heightened perception of pain in the presence of normal quantity of intestinal gas exist. Pain seems to be caused by abnormally strong contractions of the intestinal smooth muscle or by increased sensitivity of the intestine to distention. Hypersensitivity to the hormones gastrin and cholecystokinin may also be present. However, hormonal fluctuations do not correlate with symptoms. Meals of high caloric density may increase the magnitude and frequency of myoelectrical activity and gastric motility. Fat ingestion may cause a delayed peak of motor activity, which can be exaggerated in IBS. The first few days of menstruation can lead to transiently elevated prostaglandin E2, resulting in increased pain and diarrhea, probably by the release of prostaglandins.

Two major clinical types of IBS have been described. In constipation-predominant IBS, most patients have pain over at least one area of the colon and periods of constipation alternating with a more normal stool frequency. Stool often contains clear or white mucus. Pain is either colicky, coming in bouts, or a continuous dull ache; it may be relieved by a bowel movement. Eating commonly triggers symptoms. Bloating, flatulence, nausea, dyspepsia, and pyrosis can also occur.

Diarrhea-predominant IBS is characterized by precipitous diarrhea that occurs immediately on rising or during or immediately after eating, especially rapid eating. Nocturnal diarrhea is unusual. Pain, bloating, and rectal urgency are common, and incontinence may occur. Painless diarrhea is not typical.

Diagnosis is based on characteristic bowel patterns, time and character of pain, and exclusion of other disease processes through physical examination and routine diagnostic tests. Diagnostic testing should be more intensive when "red flags" are present: older age, weight loss, rectal bleeding, vomiting. Proctosigmoidoscopy with a flexible fiberoptic instrument should be performed. Introduction of the sigmoidoscope and air insufflation frequently trigger bowel spasm and pain. The mucosal and vascular patterns in IBS usually appear normal. Colonoscopy is preferred for patients >40 with a change in bowel habits, particularly those with no previous IBS symptoms, to exclude colonic polyps and tumors. In patients with chronic diarrhea, particularly older women, mucosal biopsy can rule out possible microscopic colitis.

METHODS OF THE INVENTION

The ability of an individual to metabolize a CYP3A substrate via an intestinal route is analyzed by administering an oral dose of a CYP3A substrate to an individual suffering from an enteropathic disorder, and quantitating the presence of the CYP3A substrate and/or its metabolite(s) in at least one patient sample.

In some embodiments, the method comprises identifying a patient as having an enteropathic disorder, e.g. by criteria described above for specific disease conditions; administering an oral dose of a CYP3A substrate to an individual identified as having an enteropathic disorder, and quantitating the presence of the CYP3A substrate and/or its metabolite(s) in at least one patient sample.

Patient samples include a variety of bodily fluids in which the CYP3A substrate and/or metabolites will be present, e.g. blood and derivatives thereof, urine, saliva, breath, etc. The samples will be taken prior to administration of the substrate, and at suitable time points following administration, e.g. at 15 minutes, 30 minutes, 1 hour, 1.5 hours, 2 hours, 2.5 hours, 3 hours, 4 hours, 6 hours, etc., following administration.

In some preferred embodiments, the methods of the invention are used in determining the efficacy of a therapy for treatment of an enteropathic disease, either at an individual level, or in the analysis of a group of patients, e.g. in a clinical trial format. Such embodiments typically involve the comparison of two time points for a patient or group of patients. The patient status is expected to differ between the two time points as the result of a therapeutic agent, therapeutic regimen, or disease challenge to a patient undergoing treatment.

Examples of formats for such embodiments may include, without limitation, testing enteric CYP3A metabolism at two or more time points, where a first time point is a diagnosed but untreated patient; and a second or additional time point(s) is a patient treated with a candidate therapeutic agent or regimen. An additional time point may include a patient treated with a candidate therapeutic agent or regimen, and challenged for the disease, particularly for celiac sprue and/or dermatitis herpetiformis, which may be challenged with administration of gluten.

In another format, a first time point is a diagnosed patient in disease remission, e.g. as ascertained by current clinical criteria, as a result of a candidate therapeutic agent or regimen. A second or additional time point(s) is a patient treated with a candidate therapeutic agent or regimen, and challenged with a disease-inducing agent, particularly for celiac sprue and/or dermatitis herpetiformis, which may be challenged with administration of gluten.

In such clinical trial formats, each set of time points may correspond to a single patient, to a patient group, e.g. a cohort group, or to a mixture of individual and group data. Additional control data may also be included in such clinical trial formats, e.g. a placebo group, a disease-free group, and the like, as are known in the art. Formats of interest include crossover studies, randomized, double-blind, placebo-controlled, parallel group trial is also capable of testing drug efficacy, and the like. See, for example, Clinical Trials: A Methodologic Perspective Second Edition, S. Piantadosi, Wiley-Interscience; 2005, ISBN-13: 978-0471727811; and Design and Analysis of Clinical Trials: Concepts and Methodologies, S. Chow and J. Liu, Wiley-Interscience; 2003; ISBN-13: 978-0471249856, each herein specifically incorporated by reference.

Specific clinical trials of interest include analysis of therapeutic agents for the treatment of celiac sprue and/or dermatitis herpetiformis, where a patient is identified as having celiac sprue by conventional clinical indicia. For example, in celiac sprue a daily dose of 5-10 g gluten (equivalent to 2-3 slices of bread) for two weeks can induce malabsorption, as measured by a 72-hour quantitative fecal fat collection or a D-xylose urinary test (Pyle, 2005), providing for a means to challenge the efficacy of a treatment.

In one embodiment, a blinded crossover clinical trial format is utilized. A patient alternates for a set period of time, e.g. one week, two weeks, three weeks, or from around about 7-14 days, or around about 10 days, between a test drug and placebo, with a 4-8 week washout period. The patient is challenged with gluten during both alternating time periods with around about 1 g gluten, about 5 g. gluten, about 10 g. gluten, or more, usually not more than about 25 g gluten daily. Subjects are tested with a CYP3A substrate, as described above, at the beginning and end of each alternating time period. Care is taken to ensure that subjects are not consuming other drugs or food items (e.g. grapefruit juice) that are known CYP3A4 inhibitors for an appropriate duration before the CYP3A substrate tests. The duration of gluten challenge may be about 1, about 3, about 5, about 7, about 10 days, about 14 days, because changes in the enterocytes at the villous tips are usually one of the earliest consequences of gluten exposure. By decreasing the duration of the gluten challenge or the magnitude of the daily gluten dose, adverse symptoms can be minimized.

In another embodiment a randomized, double-blind, placebo-controlled, parallel group trial is used to test drug efficacy. In one embodiment, individuals identified as having celiac sprue, who are on a gluten-free diet, undergo three sequential treatment periods, each of 1-14 day durations. Subjects will be assessed with the CYP3A substrate at entry and at the end of each treatment period. During the entire study, subjects will consume regular gluten-free meals plus drug or placebo as indicated. During the first treatment period (run-in), all subjects will receive placebo. During the second treatment period, the subjects will be randomized into drug or placebo groups. During the third treatment period, subjects will remain on the same (drug or placebo) treatment as in the second period. In addition, all subjects will receive 1-5 g gluten with each meal. Drugs that are effective will show a statistically lower frequency of relapse in the treatment arm versus placebo arm of the study.

In all such methods, the CYP3A substrate is administered at a dose that is sufficient to monitor the metabolism over time, which will vary with the specific substrate that is selected. Where the substrate is midazolam, the dose may be at least about 0.5 mg, at least about 1 mg, at least about 2 mg at least about 4 mg, at least about 5 mg, at least about 7.5 mg, and not more than about 10 mg.

The substrate may be administered in any conventional formulation, e.g. solution, suspension, tablets, powders, granules or capsules, for example, with conventional additives, such as lactose, mannitol, corn starch or potato starch; with binders, such as crystalline cellulose, cellulose derivatives, acacia, corn starch or gelatins; with disintegrators, such as corn starch, potato starch or sodium carboxymethylcellulose; with lubricants, such as talc or magnesium stearate; and if desired, with diluents, buffering agents, moistening agents, preservatives and flavoring agents.

In one embodiment of the invention, the oral formulations comprise enteric coatings, so that the active agent is delivered to the intestinal tract. Such formulations are created by coating a solid dosage form with a film of a polymer that is insoluble in acid environments, and soluble in basic environments. Exemplary films are cellulose acetate phthalate, polyvinyl acetate phthalate, hydroxypropyl methylcellulose phthalate and hydroxypropyl methylcellulose acetate succinate, methacrylate copolymers, and cellulose acetate phthalate. Other enteric formulations comprise engineered polymer microspheres made of biologically erodable polymers, which display strong adhesive interactions with gastrointestinal mucus and cellular linings and can traverse both the mucosal absorptive epithelium and the follicle-associated epithelium covering the lymphoid tissue of Peyer's patches. The polymers maintain contact with intestinal epithelium for extended periods of time and actually penetrate it, through and between cells. See, for example, Mathiowitz et al. (1997) Nature 386 (6623): 410-414. Drug delivery systems can also utilize a core of superporous hydrogels (SPH) and SPH composite (SPHC), as described by Dorkoosh et al. (2001) J Control Release 71(3):307-18.

Databases of Pharmacokinetic Analyses

Also provided are databases of pharmacokinetic analyses. Such databases will typically comprise analysis profiles of various individuals following a clinical protocol of interest etc., where such profiles are further described below.

The profiles and databases thereof may be provided in a variety of media to facilitate their use. "Media" refers to a manufacture that contains the expression profile information of the present invention. The databases of the present invention can be recorded on computer readable media, e.g. any medium that can be read and accessed directly by a computer. Such media include, but are not limited to: magnetic storage media, such as floppy discs, hard disc storage medium, and magnetic tape; optical storage media such as CD-ROM; electrical storage media such as RAM and ROM; and hybrids of these categories such as magnetic/optical storage media. One of skill in the art can readily appreciate how any of the presently known computer readable mediums can be used to create a manufacture comprising a recording of the present database information. "Recorded" refers to a process for storing information on computer readable medium, using any such methods as known in the art. Any convenient data storage structure may be chosen, based on the means used to access the stored information. A variety of data processor programs and formats can be used for storage, e.g. word processing text file, database format, etc.

As used herein, "a computer-based system" refers to the hardware means, software means, and data storage means used to analyze the information of the present invention. The minimum hardware of the computer-based systems of the present invention comprises a central processing unit (CPU), input means, output means, and data storage means. A skilled artisan can readily appreciate that any one of the currently available computer-based system are suitable for use in the present invention. The data storage means may comprise any manufacture comprising a recording of the present information as described above, or a memory access means that can access such a manufacture.

A variety of structural formats for the input and output means can be used to input and output the information in the computer-based systems of the present invention. Such presentation provides a skilled artisan with a ranking of similarities and identifies the degree of similarity contained in the test expression profile.

Reagents and Kits

Also provided are reagents and kits thereof for practicing one or more of the above-described methods. The subject reagents and kits thereof may vary greatly. Reagents of interest include reagents specifically designed for use in production of the above described analysis. Kits may include a CYP3A substrate, reagents for analysis of the substrate and/or metabolites, and such containers as are required for sample collection.

The kits may further include a software package for statistical analysis of one or more phenotypes. In addition to the above components, the subject kits will further include instructions for practicing the subject methods. These instructions may be present in the subject kits in a variety of forms, one or more of which may be present in the kit. One form in which these instructions may be present is as printed information on a suitable medium or substrate, e.g., a piece or pieces of paper on which the information is printed, in the packaging of the kit, in a package insert, etc. Yet another means would be a computer readable medium, e.g., diskette, CD, etc., on which the information has been recorded. Yet another means that may be present is a website address which may be used via the internet to access the information at a removed site. Any convenient means may be present in the kits.

The following examples are put forth so as to provide those of ordinary skill in the art with a complete disclosure and description of how to make and use the present invention, and are not intended to limit the scope of the invention or to represent that the experiments below are all or the only experiments performed. Efforts have been made to ensure accuracy with respect to numbers used (e.g., amounts, temperature, and the like), but some experimental errors and deviations may be present. Unless indicated otherwise, parts are parts by weight, molecular weight is weight average molecular weight, temperature is in degrees Centigrade, and pressure is at or near atmospheric.

Example 1

Material and Methods

Subjects.

After institutional review board approval, eight healthy adult volunteers and eight adult celiac sprue patients with diagnosed ongoing intestinal malabsorption are selected. After the initial baseline testing, celiac patients are treated with glutenase for a length of time sufficient to alleviate symptoms of malabsorption, and are then retested as done for the initial baseline analysis.

Study Design.

After the subjects fast overnight, an intravenous catheter is placed in one forearm of each subject for the withdrawal of blood. Before receiving the dose of midazolam, each subject empties his or her bladder, and a baseline blood sample is obtained. Each subject receives 4.0 mg midazolam orally as a solution. Blood samples are obtained 5, 15, 30, and 45 minutes and 1, 1.5, 2, 2.5, 3, 4, 5, 6, 8, 10, 12, and 24 hours after drug administration. Serum is obtained and frozen at $-20°$ C. until analysis. Urine is collected during the intervals 0 to 2, 2 to 4, 4 to 6, 6 to 12, and 12 to 24 hours after the dose and frozen at $-20°$ C. until analysis. Midazolam-induced sleep time is determined as the interval between the time the subject is no longer able to be aroused by mild auditory stimuli and the time that the subject remains awake and aware in response to mild auditory stimuli. A mild auditory stimulus is defined as speaking in a normal conversational voice.

Sample Analysis.

Serum samples are processed with use of a liquid-liquid extraction technique and quantified after derivatization with gas chromatography-mass spectrometry (Hewlett-Packard 597 1 mass selective detector and 5890A gas chromatograph) as described by Thummel et al. (1994) J. Pharmacol. Exp. Ther. 271:549-546, herein specifically incorporated by reference. Monitored ions include 310, and 398, which are used to quantify levels of midazolam, and 1'-hydroxymidazolam. Diazepam and temazepam are used as the internal standards for parent and metabolite, respectively, and the monitored ions are 256 and 357, respectively, after derivitization with N-methyl-N-t-butyldimethylsilyl trifluoroacetamide containing 1% t-butyldimethylchlorosilane (Regis Technologies, Morton Grove, Ill.)

The assay is used to routinely measure midazolam and metabolite concentrations of 1 ng/ml. Urine samples are processed as described after deconjugation with P-glucuronidase (Sigma Chemical Co., St. Louis, Mo.). The midazolam concentration in the infused solution is estimated by HPLC (see Gorski et al. (1994) Biochem Pharmacol 47:1643-1657, herein specifically incorporated by reference). Serum samples are processed through a liquid-liquid extraction method.

Pharmacokinetic Analysis.

Standard model independent methods are used to determine the pharmacokinetic parameters of interest. The terminal elimination rate constant (p) is determined by linear regression. The elimination half-life ($t\frac{1}{2}$) is determined as $t\frac{1}{2}=0.693/\beta$. The maximum concentration and time to reach the maximum concentration are determined by visual inspection of the data. The area under the concentration-time curve (AUC from zero to final detectable midazolam serum concentration) after oral administration is determined by a combination of linear and logarithmic trapezoidal methods with extrapolation to infinity.

The efficacy of treatment for celiac sprue patients is assessed by determining the decrease in enteric CYP3A metabolism of midazolam. An effective glutenase will protect a patient from gluten-induced enteropathy; consequently, the $t\frac{1}{2}$ and AUC for midazolam will remain unchanged before and after gluten challenge. In contrast, the placebo will result in gluten-induced enteropathy; consequently, the $t\frac{1}{2}$ and AUC for midazolam will increase after gluten challenge as compared to corresponding values before gluten challenge.

Example 2

Administration of midazolam and sample analysis is performed as described above.

Patients are identified as having celiac sprue by conventional clinical indicia.

The clinical efficacy of a prolyl endopeptidase from *Aspergillus niger* (Stepniak, et al. *Am. J. Physiol. GI Liver Physiol.* 291, 621-629, 2006) is evaluated as follows. Clinically diagnosed adult celiac patients who are on a gluten-free diet are enrolled in the study and are divided into two groups. Each subject in the clinical trial undergoes three sequential treatment periods of 1-14 day duration. CYP3A metabolism of each subject is assessed at entry and at the end of each treatment period.

During the entire study, subjects consume regular gluten-free meals plus one dose of glutenase or placebo with breakfast, lunch and dinner. The dose range of the glutenase to be tested for clinical efficacy is 0.2-10 mg/kg. During the first (run-in) period, all subjects receive placebo glutenase. It is anticipated that the intestinal health of a subset of subjects will improve due to greater dietary vigilance on their part. During the second period, the subjects are randomized into active or placebo glutenase groups. This period is designed to establish whether the intestinal health of subjects taking active glutenase improves as a result of its ability to detoxify background levels of gluten in a celiac patient's diet. During the third period, subjects will remain on the same (drug or placebo) treatment as in the second period. In addition, all subjects receive 0.5-3 g gluten with each meal in the form of an appropriate test article (e.g., a cookie or a slice or bread). The efficacy of the glutenase treatment is primarily assessed based on the results of this treatment period.

A statistically significant result is based on midazolam AUC and clearance rate measurements. An increase in AUC and a decrease in clearance rate imply that the celiac condition has worsened as a result of exposure to toxic gluten peptides. This is observed at the end of the third treatment period in subjects who are dosed with placebo glutenase. A statistically unchanged AUC and clearance rate are indicative of gluten detoxification by the oral glutenase. This is observed at the end of the third treatment period in subjects who are dosed with active glutenase. In subjects who initiate the clinical trial with evidence of active disease, a decrease in AUC and increase in clearance rate may be observed at the end of the second period relative to the end of the first period. A two-fold or higher change in AUC or clearance between the two cohorts is anticipated for statistical significance.

Example 3

An alternate method for assessing the efficacy of the prolyl endopeptidase from *Aspergillus niger* involves a double-blind, placebo controlled crossover clinical trial. The principal advantage of this trial format is that each patient serves as his/her own control. Clinically diagnosed adult celiac patients whose disease is in remission (as judged by a normal small bowel biopsy, seronegativity, and a 72-hour fecal fat measurement within the normal range) are enrolled in the study.

Each subject in the clinical trial undergoes two treatment periods of 1-14 day durations separated by a 4-8 week washout. CYP3A metabolism of each subject is assessed at entry and at the end of each treatment period. During each of the two treatment periods, subjects receive 0.5-3 g gluten with each meal in the form of an appropriate test article. Each subject receives active glutenase and placebo glutenase alternately in the two treatment periods; the order of dosing is randomly assigned. The dose range of the glutenase to be tested for clinical efficacy is 0.2-10 mg/kg.

A statistically significant result is based on midazolam AUC and clearance rate measurements. An increase in AUC and a decrease in clearance rate imply that the celiac condition has worsened as a result of exposure to toxic gluten peptides. This is observed at the end of the placebo glutenase treatment period. A statistically unchanged AUC and clearance rate are indicative of gluten detoxification by the oral glutenase. This is observed at the end of the active glutenase treatment period.

Example 4

An alternate glutenase therapy is a two-enzyme glutenase comprised of protease EP-B2 from barley and peptidase SC PEP from *Sphingomonas capsulata* (Gass, et al., *Gastroenterology* 133, 472-480, 2007). The clinical efficacy of this enzyme is tested via a clinical trial, as in Example 2 or Example 3 above. In one embodiment, glutenase doses in the range of 0.2-10 mg/kg, with the two proteins present in a 1:1 mass ratio, are tested for efficacy by the methods of the invention.

Example 5

An alternate drug candidate for celiac sprue is the intestinal permeability inhibitor, AT1001 (Paterson, et al. *Aliment. Pharmacol. Ther.* 26, 757-766, 2007). The clinical efficacy of this drug is tested via a clinical trial, as in Example 2 or Example 3 above. In one embodiment, the doses in the range of 5 to 50 mg/kg (tid, with meals) are tested for efficacy by the methods of the invention.

Example 6

Material and Methods

Subjects.

After institutional review board approval, eight healthy adult volunteers and eight adult celiac sprue patients with diagnosed ongoing intestinal malabsorption are selected. After the initial baseline testing, celiac patients are treated with glutenase for a length of time sufficient to alleviate symptoms of malabsorption, and are then retested as done for the initial baseline analysis.

Study Design.

After the subjects fast overnight, an intravenous catheter is placed in one forearm of each subject for the withdrawal of blood. Before receiving the dose of midazolam, each subject empties his or her bladder, and a baseline blood sample is obtained. Each subject receives from 20 to 100 mg simvastatin orally as a solution. Blood samples are obtained 5, 15, 30, and 45 minutes and 1, 1.5, 2, 2.5, 3, 4, 5, 6, 8, 10, 12, and 24 hours after drug administration. Serum is obtained and frozen at −20° C. until analysis. Urine is collected during the intervals 0 to 2, 2 to 4, 4 to 6, 6 to 12, and 12 to 24 hours after the dose and frozen at −20° C. until analysis.

Sample Analysis.

Serum samples are processed with use of a liquid-liquid extraction technique and quantified after derivatization with gas chromatography-mass spectrometry (Hewlett-Packard 597 1 mass selective detector and 5890A gas chromatograph) as described by Thummel et al. (1994) *J. Pharmacol. Exp. Ther.* 271:549-546, herein specifically incorporated by reference. Simvastatin, 3'-hydroxy simvastatin, 6'-exomethylene simvastatin, 3',5'-dihydrodiol simvastatin, and/or simvastatin (β)-hydroxy acid are monitored.

The assay is used to routinely measure simvastatin and metabolite concentrations of 1 ng/ml. Urine samples are processed as described after deconjugation with P-glucuronidase (Sigma Chemical Co., St. Louis, Mo.). The simvastatin concentration in the infused solution is estimated by HPLC (see Gorski et al. (1994) Biochem Pharmacol 47:1643-1657, herein specifically incorporated by reference). Serum samples are processed through a liquid-liquid extraction method.

Pharmacokinetic Analysis.

Standard model independent methods are used to determine the pharmacokinetic parameters of interest. The terminal elimination rate constant (p) is determined by linear regression. The elimination half-life (t½) is determined as t½=0.693/β. The maximum concentration and time to reach the maximum concentration are determined by visual inspection of the data. The area under the concentration-time curve (AUC from zero to final detectable simvastatin serum concentration) after oral administration is determined by a combination of linear and logarithmic trapezoidal methods with extrapolation to infinity. The Cmax is determined.

The efficacy of treatment for celiac sprue patients is assessed by determining the decrease in enteric CYP3A metabolism of simvastatin. An effective glutenase will protect a patient from gluten-induced enteropathy; consequently, the t½ and AUC for simvastatin will remain unchanged before and after gluten challenge. In contrast, the placebo will result in gluten-induced enteropathy; consequently, the t½ and AUC for simvastatin will increase after gluten challenge as compared to corresponding values before gluten challenge.

Example 7

Administration of simvastatin and sample analysis is performed as described above.

Patients are identified as having celiac sprue by conventional clinical indicia.

The clinical efficacy of a prolyl endopeptidase from *Aspergillus niger* (Stepniak, et al. *Am. J. Physiol. GI Liver Physiol.* 291, 621-629, 2006) is evaluated as follows. Clinically diagnosed adult celiac patients who are on a gluten-free diet are enrolled in the study and are divided into two groups. Each subject in the clinical trial undergoes three sequential treatment periods of 1-14 day duration. CYP3A metabolism of each subject is assessed at entry and at the end of each treatment period.

During the entire study, subjects consume regular gluten-free meals plus one dose of glutenase or placebo with breakfast, lunch and dinner. The dose range of the glutenase to be tested for clinical efficacy is 0.2-10 mg/kg. During the first (run-in) period, all subjects receive placebo glutenase. It is anticipated that the intestinal health of a subset of subjects will improve due to greater dietary vigilance on their part. During the second period, the subjects are randomized into active or placebo glutenase groups. This period is designed to establish whether the intestinal health of subjects taking active glutenase improves as a result of its ability to detoxify background levels of gluten in a celiac patient's diet. During the third period, subjects will remain on the same (drug or placebo) treatment as in the second period. In addition, all subjects receive 0.5-3 g gluten with each meal in the form of an appropriate test article (e.g., a cookie or a slice or bread). The efficacy of the glutenase treatment is primarily assessed based on the results of this treatment period.

A statistically significant result is based on simvastatin AUC, Cmax, and clearance rate measurements. An increase in AUC and a decrease in clearance rate imply that the celiac condition has worsened as a result of exposure to toxic gluten peptides. This is observed at the end of the third treatment period in subjects who are dosed with placebo glutenase. A statistically unchanged AUC and clearance rate are indicative of gluten detoxification by the oral glutenase. This is observed at the end of the third treatment period in subjects who are dosed with active glutenase. In subjects who initiate the clinical trial with evidence of active disease, a decrease in AUC and increase in clearance rate may be observed at the end of the second period relative to the end of the first period. A two-fold or higher change in AUC or clearance between the two cohorts is anticipated for statistical significance.

Example 8

An alternate method for assessing the efficacy of the prolyl endopeptidase from *Aspergillus niger* involves a double-blind, placebo controlled crossover clinical trial. The principal advantage of this trial format is that each patient serves as his/her own control. Clinically diagnosed adult celiac patients whose disease is in remission (as judged by a normal small bowel biopsy, seronegativity, and a 72-hour fecal fat measurement within the normal range) are enrolled in the study.

Each subject in the clinical trial undergoes two treatment periods of 1-14 day durations separated by a 4-8 week washout. CYP3A metabolism of each subject is assessed at entry and at the end of each treatment period. During each of the two treatment periods, subjects receive 0.5-3 g gluten with each meal in the form of an appropriate test article. Each subject receives active glutenase and placebo glutenase alternately in the two treatment periods; the order of dosing is randomly assigned. The dose range of the glutenase to be tested for clinical efficacy is 0.2-10 mg/kg.

A statistically significant result is based on simvastatin AUC, Cmax, and clearance rate measurements. An increase in AUC and a decrease in clearance rate imply that the celiac condition has worsened as a result of exposure to toxic gluten peptides. This is observed at the end of the placebo glutenase treatment period. A statistically unchanged AUC and clearance rate are indicative of gluten detoxification by the oral glutenase. This is observed at the end of the active glutenase treatment period.

Example 9

An alternate glutenase therapy is a two-enzyme glutenase comprised of protease EP-B2 from barley and peptidase SC PEP from *Sphingomonas capsulata* (Gass, et al., *Gastroenterology* 133, 472-480, 2007). The clinical efficacy of this enzyme is tested via a clinical trial, as in Example 7 or Example 8 above. In one embodiment, glutenase doses in the range of 0.2-10 mg/kg, with the two proteins present in a 1:1 mass ratio, are tested for efficacy by the methods of the invention.

Example 10

An alternate drug candidate for celiac sprue is the intestinal permeability inhibitor, AT1001 (Paterson, et al. *Aliment. Pharmacol. Ther.* 26, 757-766, 2007). The clinical efficacy of this drug is tested via a clinical trial, as in Example 7 or Example 8 above. In one embodiment, the doses in the range of 5 to 50 mg/kg (tid, with meals) are tested for efficacy by the methods of the invention.

These and other diagnostic methods of the invention can be practiced using the methods provided by the invention.

All publications, patents, and patent applications cited in this specification are herein incorporated by reference as if each individual publication, patent, or patent application were specifically and individually indicated to be incorporated by reference.

The present invention has been described in terms of particular embodiments found or proposed by the inventor to comprise preferred modes for the practice of the invention. It will be appreciated by those of skill in the art that, in light of the present disclosure, numerous modifications and changes can be made in the particular embodiments exemplified without departing from the intended scope of the invention. Moreover, due to biological functional equivalency considerations, changes can be made in methods, structures, and compounds without affecting the biological action in kind or amount. All such modifications are intended to be included within the scope of the appended claims.

What is claimed is:

1. A non-invasive method for assessing the efficacy of a clinical regimen in the treatment of an individual with an intolerance to gluten, the method comprising:
    identifying an individual as having an intolerance to gluten undergoing treatment with a clinical regimen of interest;
    administering an oral dose of a CYP3A substrate to the individual,
    quantitating a post dose concentration of the CYP3A substrate and/or its metabolite(s) in at least one sample from the individual, selected from the group consisting of blood, saliva, urine and breath;
    assessing efficacy of the regimen, wherein an efficacious regimen protects from gluten-induced enteropathy that results in decreased enteric metabolism of the CYP3A substrate relative to a gluten-tolerant control sample, to generate an analysis of efficacy; and
    providing the analysis of the efficacy of the clinical regimen, wherein the extent of metabolism of the CYP3A substrate to its metabolite, indicated by said post-dose concentration, is a non-invasive surrogate for the efficacy of the clinical regimen in protecting the individual from gluten-induced enteropathy.

2. The method of claim 1, wherein the individual is a human.

3. The method of claim 1, wherein the CYP3A substrate is midazolam.

4. The method of claim 3, wherein the presence of midazolam, 1'-hydroxymidazolam, and/or 4-hydroxymidozalam is quantitated in a sample from the individual.

5. The method of claim 1, where the CYP3A substrate is simvastatin.

6. The method of claim 1, wherein the steps of administering a CYP3A substrate and quantitating the presence of the CYP3A substrate and/or its metabolite(s) in at least one sample from the individual are performed at two or more time points, where the disease status of the individual is expected to differ between the time points as the result of administering the clinical regimen to the individual.

7. The method of claim 1, wherein the individual is one of a group of individuals in a clinical trial.

8. The method of claim 7, wherein the clinical trial is a crossover trial.

9. The method of claim 7, wherein the clinical trial is a double blinded parallel trial.

10. The method of claim 1, wherein the efficacy of treatment for an individual with an intolerance to gluten is assessed by determining the decrease in enteric CYP3A metabolism of the CYP3A substrate, wherein an effective treatment protects from gluten-induced enteropathy and an area under a concentration-time curve (AUC) for the CYP3A substrate will remain unchanged after gluten challenge; and for an ineffective treatment the AUC for the CYP3A substrate will increase after gluten Challenge.

11. The method of claim 1, wherein the efficacy of treatment for an individual with an intolerance to gluten is assessed by determining the decrease in enteric CYP3A metabolism of the CYP3A substrate, wherein an effective treatment protects from gluten-induced enteropathy and a maximum concentration ($C_{max}$) for the CYP3A substrate will remain unchanged after gluten challenge; and for an ineffective treatment the $C_{max}$ for the CYP3A substrate will increase after gluten challenge.

12. The method of claim 1, wherein the efficacy of treatment for an individual with an intolerance to gluten is assessed by determining the decrease in enteric CYP3A metabolism of simvastatin, wherein an effective treatment protects from gluten-induced enteropathy and a maximum concentration ($C_{max}$) for simvastatin will remain unchanged after gluten challenge; and for an ineffective treatment the $C_{max}$ for simvastatin will increase after gluten challenge.

13. A non-invasive method for assessing the efficacy of a clinical regimen in the treatment of an individual with an intolerance to gluten, the method comprising:
    identifying an individual as having an intolerance to gluten undergoing treatment with a clinical regimen of interest;
    administering an oral dose of simvastatin to the individual;
    measuring serum concentration from 30 minutes to 3 hours post-dose of simvastatin, 3'-hydroxy simvastatin, 6'-exomethylene simvastatin, 3',5'-dihydrodiol simvastatin, and/or simvastatin (β)-hydroxy acid in at least one sample from the individual;
    assessing efficacy of the regimen, wherein an efficacious regimen protects from gluten-induced enteropathy that results in decreased enteric metabolism of the simvastatin relative to a gluten-tolerant control sample, to generate an analysis of efficacy; and
    providing the analysis of the efficacy of the clinical regimen, wherein the extent of simvastatin metabolism, indicated by said post-dose concentration, is a non-invasive surrogate for the efficacy of the clinical regimen in protecting the individual from gluten-induced enteropathy.

14. The method of claim 13, wherein the efficacy of treatment for an individual with an intolerance to gluten is assessed by determining the decrease in enteric CYP3A metabolism of the simvastatin, wherein an effective treatment protects from gluten-induced enteropathy and an area under a concentration-time curve (AUC) for simvastatin will remain unchanged after gluten challenge; and for an ineffective treatment the AUC for simvastatin will increase after gluten challenge.

15. A non-invasive method for clinical management of an individual with an intolerance to gluten, the method comprising:
    identifying an individual as having an intolerance to gluten undergoing treatment with a current clinical regimen of interest;
    administering an oral dose of simvastatin to the individual;
    measuring serum concentration from 30 minutes to 3 hours post-dose of simvastatin, 3'-hydroxy simvastatin, 6'-exomethylene simvastatin, 3',5'-dihydrodiol simvastatin, and/or simvastatin (β)hydroxy acid in at least one sample from the individual;

assessing efficacy of the current regimen, wherein an efficacious regimen protects from gluten-induced enteropathy that results in decreased enteric metabolism of the simvastatin relative to a gluten-tolerant control sample; and providing a clinical regimen to the individual in accordance with an analysis of the efficacy of the current clinical regimen wherein the extent of simvastatin metabolism, indicated by said post-dose concentration, is a non-invasive surrogate for the efficacy of the current clinical regimen in protecting the individual from gluten-induced enteropathy.

* * * * *